(12) United States Patent
Gupta et al.

(10) Patent No.: US 11,406,412 B2
(45) Date of Patent: Aug. 9, 2022

(54) ATHERECTOMY CATHETERS WITH IMAGING

(71) Applicant: Avinger, Inc., Redwood City, CA (US)

(72) Inventors: Priyanshu Gupta, Palo Alto, CA (US); Michael Zung, San Carlos, CA (US); Charles W. McNall, Cottonwood Heights, UT (US); Himanshu N. Patel, San Jose, CA (US); Christina Van, San Leandro, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 14/401,175

(22) PCT Filed: Mar. 15, 2013

(86) PCT No.: PCT/US2013/031901
§ 371 (c)(1),
(2) Date: Nov. 14, 2014

(87) PCT Pub. No.: WO2013/172970
PCT Pub. Date: Nov. 21, 2013

(65) Prior Publication Data
US 2015/0141816 A1 May 21, 2015

Related U.S. Application Data

(60) Provisional application No. 61/646,843, filed on May 14, 2012.

(51) Int. Cl.
*A61B 17/32* (2006.01)
*A61B 5/00* (2006.01)
(Continued)

(52) U.S. Cl.
CPC ...... *A61B 17/32002* (2013.01); *A61B 1/0017* (2013.01); *A61B 1/00087* (2013.01);
(Continued)

(58) Field of Classification Search
CPC ....... A61B 2017/320791; A61B 2017/320032; A61B 17/320758; A61B 2090/3735;
(Continued)

(56) References Cited

U.S. PATENT DOCUMENTS 3,367,727 A 2/1968 Ward et al.
3,908,637 A 9/1975 Doroshow
(Continued)

FOREIGN PATENT DOCUMENTS

CN 1875242 A 12/2006
CN 1947652 A 4/2007
(Continued)

OTHER PUBLICATIONS

Simpson et al.; U.S. Appl. No. 14/424,266 entitled "Re-entry stylet for catheter," filed Feb. 26, 2015.
(Continued)

*Primary Examiner* — Ashley K Buran
*Assistant Examiner* — Helene Bor
(74) *Attorney, Agent, or Firm* — Shay Glenn LLP

(57) ABSTRACT

An atherectomy catheter includes an elongate flexible catheter body, an elongate deflectable distal tip coupled to the catheter body at a hinge point, a rotatable cutter near the distal end of the catheter body, and a drive shaft extending within the catheter body and configured to rotate the cutter. The atherectomy catheter further includes an optical fiber extending through the drive shaft substantially on-axis with the catheter body and attached to the cutter. The optical fiber is configured to rotate with the drive shaft. The atherectomy catheter further includes a wedge configured to deflect the distal tip away from the catheter body at the hinge point upon axial movement of the drive shaft.

23 Claims, 12 Drawing Sheets

(51) Int. Cl.
*A61B 1/00* (2006.01)
*A61B 17/3207* (2006.01)
*A61B 1/313* (2006.01)
*A61B 90/00* (2016.01)

(52) U.S. Cl.
CPC ...... *A61B 1/00133* (2013.01); *A61B 1/00165* (2013.01); *A61B 1/3137* (2013.01); *A61B 5/0066* (2013.01); *A61B 5/0084* (2013.01); *A61B 17/320783* (2013.01); *A61B 17/320758* (2013.01); *A61B 2017/320032* (2013.01); *A61B 2017/320791* (2013.01); *A61B 2090/3614* (2016.02); *A61B 2090/3735* (2016.02)

(58) Field of Classification Search
CPC .... A61B 2090/3614; A61B 17/320783; A61B 5/0084; A61B 5/0066; A61B 1/3137; A61B 1/0017; A61B 1/00165; A61B 1/00133; A61B 1/00087; A61B 17/32002
See application file for complete search history.

(56) References Cited

U.S. PATENT DOCUMENTS

| | | | |
|---|---|---|---|
| 4,178,935 A | 12/1979 | Gekhaman et al. | |
| 4,487,206 A | 12/1984 | Aagard | |
| 4,527,553 A * | 7/1985 | Upsher | A61B 1/07 600/188 |
| 4,552,554 A | 11/1985 | Gould et al. | |
| 4,578,061 A | 3/1986 | Lemelson | |
| 4,611,600 A | 9/1986 | Cohen | |
| 4,621,353 A | 11/1986 | Hazel et al. | |
| 4,639,091 A | 1/1987 | Huignard et al. | |
| 4,651,753 A | 3/1987 | Lifton | |
| 4,654,024 A | 3/1987 | Crittenden et al. | |
| 4,681,106 A | 7/1987 | Kensey et al. | |
| 4,686,982 A | 8/1987 | Nash | |
| 4,691,708 A | 9/1987 | Kane | |
| 4,729,763 A | 3/1988 | Henrie | |
| 4,771,774 A | 9/1988 | Simpson et al. | |
| 4,781,186 A | 11/1988 | Simpson et al. | |
| 4,841,977 A | 6/1989 | Griffith et al. | |
| 4,857,046 A | 8/1989 | Stevens et al. | |
| 4,920,961 A | 5/1990 | Grossi et al. | |
| 4,926,858 A | 5/1990 | Gifford, III et al. | |
| 5,000,185 A | 3/1991 | Yock | |
| 5,018,529 A | 5/1991 | Tenerz et al. | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,366,464 A | 11/1994 | Belknap | |
| 5,372,601 A | 12/1994 | Lary | |
| 5,383,460 A | 1/1995 | Jang et al. | |
| 5,383,467 A | 1/1995 | Auer et al. | |
| 5,425,273 A | 6/1995 | Chevalier | |
| 5,429,136 A * | 7/1995 | Milo | A61B 8/12 600/439 |
| 5,431,673 A | 7/1995 | Summers et al. | |
| 5,437,284 A | 8/1995 | Trimble | |
| 5,459,570 A | 10/1995 | Swanson et al. | |
| 5,460,168 A | 10/1995 | Masubuchi et al. | |
| 5,465,147 A | 11/1995 | Swanson | |
| 5,507,725 A * | 4/1996 | Savage | A61M 25/0147 604/95.04 |
| 5,507,760 A | 4/1996 | Wynne et al. | |
| 5,507,795 A | 4/1996 | Chiang et al. | |
| 5,517,998 A | 5/1996 | Madison | |
| 5,556,405 A | 9/1996 | Lary | |
| 5,607,394 A | 3/1997 | Andersen et al. | |
| 5,620,426 A | 4/1997 | Braithwaite | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,749,846 A | 5/1998 | Edwards et al. | |
| 5,795,295 A | 8/1998 | Hellmuth et al. | |
| 5,807,339 A | 9/1998 | Bostrom et al. | |
| 5,830,145 A | 11/1998 | Tenhoff | |
| 5,836,957 A | 11/1998 | Schulz et al. | |
| 5,843,050 A | 12/1998 | Jones et al. | |
| 5,843,103 A | 12/1998 | Wulfman | |
| 5,851,212 A | 12/1998 | Zirps et al. | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,938,602 A | 8/1999 | Lloyd | |
| 5,938,671 A | 8/1999 | Katoh et al. | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,285,903 B1 | 9/2001 | Rosenthal et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,375,615 B1 | 4/2002 | Flaherty et al. | |
| 6,402,719 B1 | 6/2002 | Ponzi et al. | |
| 6,416,527 B1 | 7/2002 | Berg et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,717 B1 | 9/2002 | Pantages et al. | |
| 6,454,779 B1 | 9/2002 | Taylor | |
| 6,482,216 B1 | 11/2002 | Hiblar et al. | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |

(56) References Cited

U.S. PATENT DOCUMENTS

| | | |
|---|---|---|
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,333,007 B2 | 5/2016 | Escudero et al. |
| 9,345,511 B2 | 5/2016 | Smith et al. |
| 9,351,757 B2 | 5/2016 | Kusleika |
| 9,579,157 B2 | 2/2017 | Moberg |
| 10,406,316 B2 | 9/2019 | Garvey et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0077642 A1* | 6/2002 | Patel ............... A61B 17/320758 606/167 |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |

(56) References Cited

U.S. PATENT DOCUMENTS

| | | |
|---|---|---|
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 * | 8/2005 | Maschke .............. A61B 5/0066 606/159 |
| 2005/0192496 A1 | 9/2005 | Maschke |
| 2005/0197623 A1 * | 9/2005 | Leeflang ............ A61B 1/00078 604/95.04 |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 * | 2/2006 | Simpson ................ A61B 10/02 128/898 |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Amal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 * | 11/2007 | Rosenthal ........ A61B 17/32002 606/159 |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 * | 8/2009 | Lee ................ A61B 17/320758 604/22 |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |

(56) References Cited

U.S. PATENT DOCUMENTS

| | | |
|---|---|---|
| 2010/0317973 A1 | 12/2010 | Nita |
| 2010/0324472 A1 | 12/2010 | Wulfman |
| 2011/0004107 A1* | 1/2011 | Rosenthal ...... A61B 17/320758 600/479 |
| 2011/0021926 A1 | 1/2011 | Spencer et al. |
| 2011/0023617 A1 | 2/2011 | Miao et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0035692 A1 | 2/2013 | Sorensen et al. |
| 2013/0065124 A1* | 3/2013 | Morishima ....... H01M 10/0585 429/211 |
| 2013/0072787 A1 | 3/2013 | Wallace et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0213893 A1 | 7/2014 | Simpson et al. |
| 2014/0222042 A1 | 8/2014 | Kessler et al. |
| 2014/0222047 A1 | 8/2014 | Vreeman |
| 2014/0275996 A1 | 9/2014 | Stigall |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0164530 A1 | 6/2015 | Carver et al. |
| 2016/0192962 A1 | 7/2016 | Simpson et al. |
| 2016/0199092 A1 | 7/2016 | Patel et al. |
| 2017/0065293 A1 | 3/2017 | Rosenthal et al. |
| 2017/0065295 A1 | 3/2017 | Patel et al. |
| 2018/0042520 A1 | 2/2018 | Patel et al. |
| 2018/0049700 A1 | 2/2018 | Black et al. |
| 2018/0192880 A1 | 7/2018 | Patel et al. |
| 2018/0207417 A1 | 7/2018 | Zung et al. |
| 2018/0256187 A1 | 9/2018 | Patel et al. |
| 2022/0039828 A1 | 2/2022 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | 05103763 A | 4/1993 |
| JP | H06-027343 A | 2/1994 |
| JP | H07184888 A | 7/1995 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005230550 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 200783057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016068758 A | 3/2016 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO2010/039464 A1 | 4/2010 |

(56) References Cited

FOREIGN PATENT DOCUMENTS

| | | |
|---|---|---|
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO 2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2019/204797 A1 | 10/2019 |

OTHER PUBLICATIONS

Simpson et al.; U.S. Appl. No. 14/424,277 entitled "Balloon atherectomy catheters with imaging," filed Feb. 26, 2015.

Newhauser et al.; U.S. Appl. No. 14/433,786 entitled "Occusion-crossing devices," filed Apr. 6, 2015.

Gupta et al.; U.S. Appl. No. 14/776,749 entitled "Tissue collection device for catheter," filed Sep. 15, 2015.

Smith et al.; U.S. Appl. No. 14/776,750 entitled "Chronic total occlusion crossing devices with imaging," filed Sep. 15, 2015.

Smith et al.; U.S. Appl. No. 14/776,748 entitled "Optical pressure sensor assembly," filed Sep. 15, 2015.

Simpson et al.; U.S. Appl. No. 14/899,877 entitled "Occusion sheath for imaging catheter," filed Dec. 18, 2015.

Simpson et al.; U.S. Appl. No. 14/899,893 entitled "Identification of elastic lamina to guide interventional therapy," filed Dec. 18, 2015.

Aziz et al.; Chronic total occlusions—a stiff challege requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Kankaria; U.S. Appl. No. 14/400,140 entitled "Optical coherence tomography with index fiber for biological imaging," filed Nov. 10, 2014.

Tachibana et al.; U.S. Appl. No. 14/400,151 entitled "Atherectomy catheter drive assemblies," filed Nov. 10, 2014.

Patel et al.; U.S. Appl. No. 15/162,330 entitled "Atherectomy catheters with longitudinally displaceable drive shafts," filed May 23, 2016.

Spencer et al.; U.S. Appl. No. 15/162,353 entitled "Occlusion-crossing devices, atherectomy devices, and imaging," filed May 23, 2016.

Tachibana et al.; U.S. Appl. No. 15/162,391 entitled "Atherectomy catheter drive assemblies," filed May 23, 2016.

Shinkle et al.; Evaluation of stent placement and outcomes with optical coherence tomography; Interv. Cardiol.; 2(4); pp. 535-543; (manuscript version, 12 pages); Aug. 2010.

Patel et al.; U.S. Appl. No. 15/324,325 entitled "High speed chronic total occulusion crossing devices," filed Jan. 6, 2017.

Kankaria; U.S. Appl. No. 15/419,815 entitled "Optical coherence tomography with graded index fiber for biological imaging," filed Jan. 30, 2017.

Simpson et al.; U.S. Appl. No. 15/434,758 entitled "Occlusion-crossing devices, imaging, and atherectomy devices," filed Feb. 16, 2017.

Simpson et al.; U.S. Appl. No. 15/457,960 entitled "Atherectomy catheters devices having multi-channel bushings," filed Mar. 13, 2017.

Smith et al.; U.S. Appl. No. 15/854,579 entitled "Chronic total occasion crossing devices with imaging," filed Dec. 26, 2017.

Newhauser et al.; U.S. Appl. No. 15/954,407 entitled "Occlusion-crossing devices," filed Apr. 16, 2018.

Christensen; U.S. Appl. No. 16/069,545 entitled "OCT imaging catheter with lag correction," filed Jul. 12, 2018.

Rosenthal et al.; U.S. Appl. No. 16/105,743 entitled "Atherectomy catheter with laterally-displaceable tip," filed Aug. 20, 2018.

Patel et al.; U.S. Appl. No. 16/148,246 entitled "Atherectomy catheter with serrated cutter," filed Oct. 1, 2018.

Simpson et al.; U.S. Appl. No. 16/194,183 entitled "Indetification of elastic lamina to guide interventional therapy," filed Nov. 16, 2018.

Fernandez et al., U.S. Appl. No. 16/305,136 entitled "Catheter device with detachable distal end," filed Nov. 28, 2018.

Patel et al., U.S. Appl. No. 16/310,470 entitled "Atherectomy catheter with shapeable distal tip," filed Dec. 17, 2019.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Leitgeb et al.; Performance of fourier domain vs time domain optical coherence tomography; Optics Express; 11(8); pp. 889-894; Apr. 21, 2003.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical esperiences; Cardiovascular and Interventional Radiology; Sprinver-Verlag; 22(6); pp. 504-509; Nov. 1, 1999.

Tachibana et al.; U.S. Appl. No. 16/372,112 entitled "Atherectomy catheter drive assemblies," filed Apr. 1, 2019.

Radjabi et al.; U.S. Appl. No. 16/347,840 entitled "Methods, systems and apparatuses for displaying real-time catheter position," filed May 7, 2019.

Stamper et al.; Plaque characterization with optical coherence tomography. Journal of the American College of Cardiology. 47(8); pp. 69-79; Apr. 18, 2006.

Patel et al.; U.S. Appl. No. 16/490,903 entitled "Atherctomy catheter," filed Jul. 2, 2019.

Black et al.; U.S. Appl. No. 16/506,851 entitled "Optical coherence tomography for biological imaging," filed Jul. 9, 2019.

Patel et al.; U.S. Appl. No. 16/516,093 entitled "High speed chronic total occlusion crossing devices," filed Jul. 18, 2019.

Patel et al.; U.S. Appl. No. 16/681,807 entitled "Atherectomy catheters and occlusion crossing devices," filed Nov. 12, 2019.

Bayer Material Science:: Snap-Fit Joints for Plastics; 26 pages; retrieved from the internet: ( https://web.archive.org/web/20121119232733if_/http://fab.cba.mit.edu:80/classes/S62.12/people/vemelle.noel/Plastic_Snap_fit_design.pdf) on Sep. 26, 2018.

Sharma et al.; Common-path optical coherence tomography with side-viewing bare fiber probe for endoscopic optical coherence tomography; vol. 78; 113102; 5 pages; Nov. 6, 2007.

Patel et al.; U.S. Appl. No. 16/801,047 entitled "Micro-molded anamorphic reflector lens for image guided therapeutic/diagnostic catheters," filed Feb. 25, 2020.

(56) References Cited

OTHER PUBLICATIONS

Smith et al.; U.S. Appl. No. 16/941,310 entitled "Chronic total occlusion crossing devices with imaging," filed Jul. 28, 2020.
Spencer et al.; U.S. Appl. No. 16/943,446 entitled "Catheter-based off-axis optical coherence tomography imaging system," filed Jul. 30, 2020.
Patel et al.; U.S. Appl. No. 17/046,066 entitled "Occlusion-crossing devices," filed Oct. 8, 2020.
Simpson et al.; U.S. Appl. No. 17/075,548 entitled "Identification of elastic lamina to guide interventional therapy," filed Oct. 20, 2020.
Smith et al.; U.S. Appl. No. 17/189,123 entitled "Optical pressure sensor assembly," filed Mar. 1, 2021.
Kankaria; U.S. Appl. No. 17/209,162 entitled "Optical coherence tomography with graded index fiber for biological imaging," filed Mar. 22, 2021.
Newhauser et al.; U.S. Appl. No. 17/209,168 entitled "Occlusion-crossing devices," filed Mar. 22, 2021.
Patel et al.; U.S. Appl. No. 17/34/,419 entitled "Micro-molded anamorphic reflector lens for image guided therapeutic/diagnostic catheters," filed Jun. 14, 2021.
Patel et al.; U.S. Appl. No. 17/443,398 entitled "Guidewire positioning catheter," filed Jul. 26, 2021.
Gupta et al.; U.S. Appl. No. 17/445,648 entitled "Tissue collection device for catheter," filed Aug. 23, 2021.
Simpson et al.; U.S. Appl. No. 17/449,867 entitled "Occlusion-crossing devices, imaging, and atherectomy devices," filed Oct. 4, 2021.
Spencer et al.; U.S. Appl. No. 17/449,895 entitled "Occlusion-crossing devices, atherectomy devices, and imaging," filed Oct. 4, 2021.
Patel et al.; U.S. Appl. No. 17/455,655 entitled "Atherectomy catheter with shapeable distal tip," filed Nov. 18, 2021.
Merriam Webster; Proximal (Definition); 10 pages; retrieved from the internet (https://www.merriam-webster.com/dictionary/proximal) on Jun. 9, 2021.
Wikipedia; Hinge; 4 pages; retrieved from the internet (https://en.wikipedia.org/w/index.php?title=Hinge&oldid=479569345) on Jun. 9, 2021.

\* cited by examiner

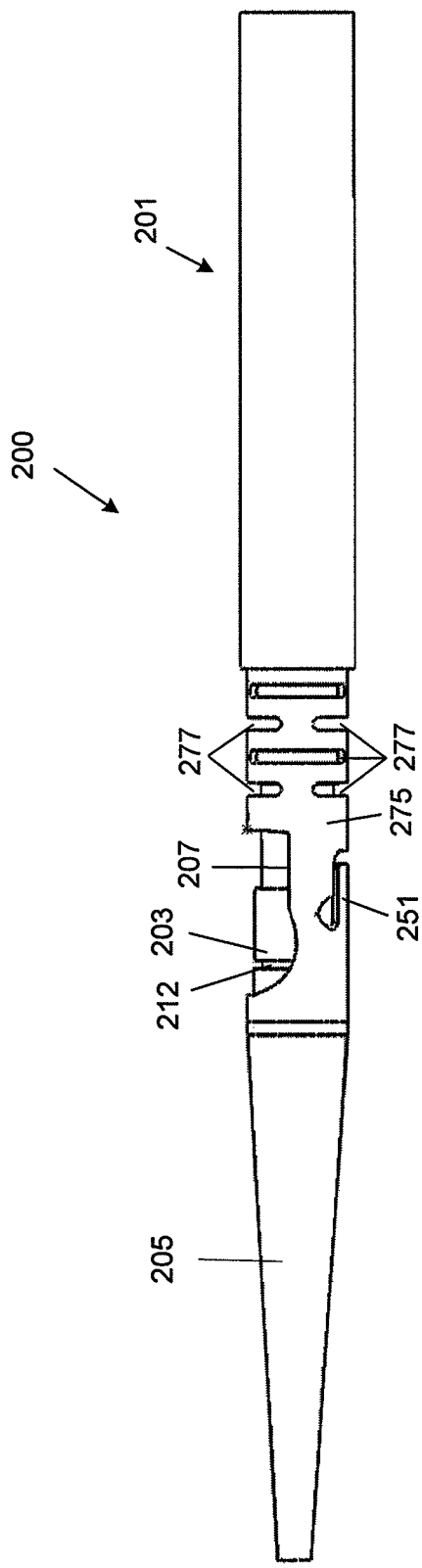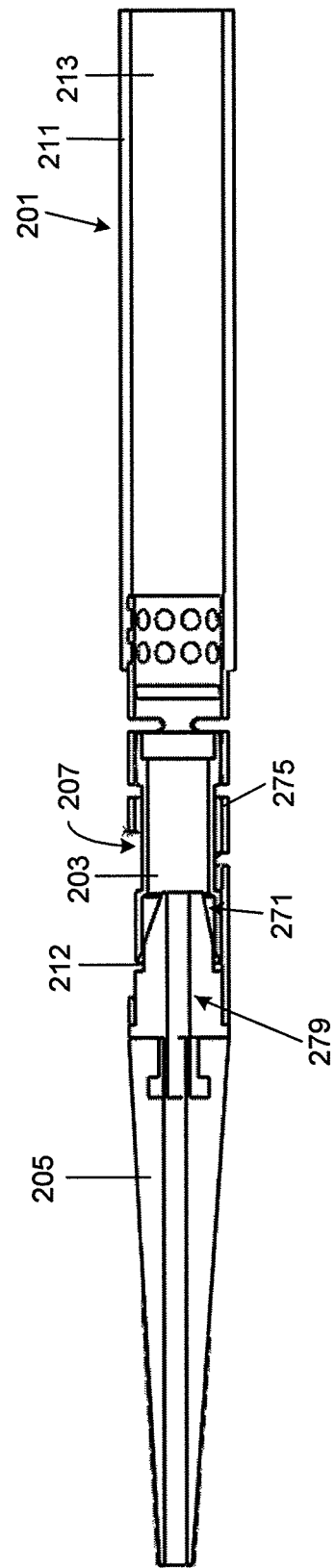
FIG. 3A
FIG. 3B

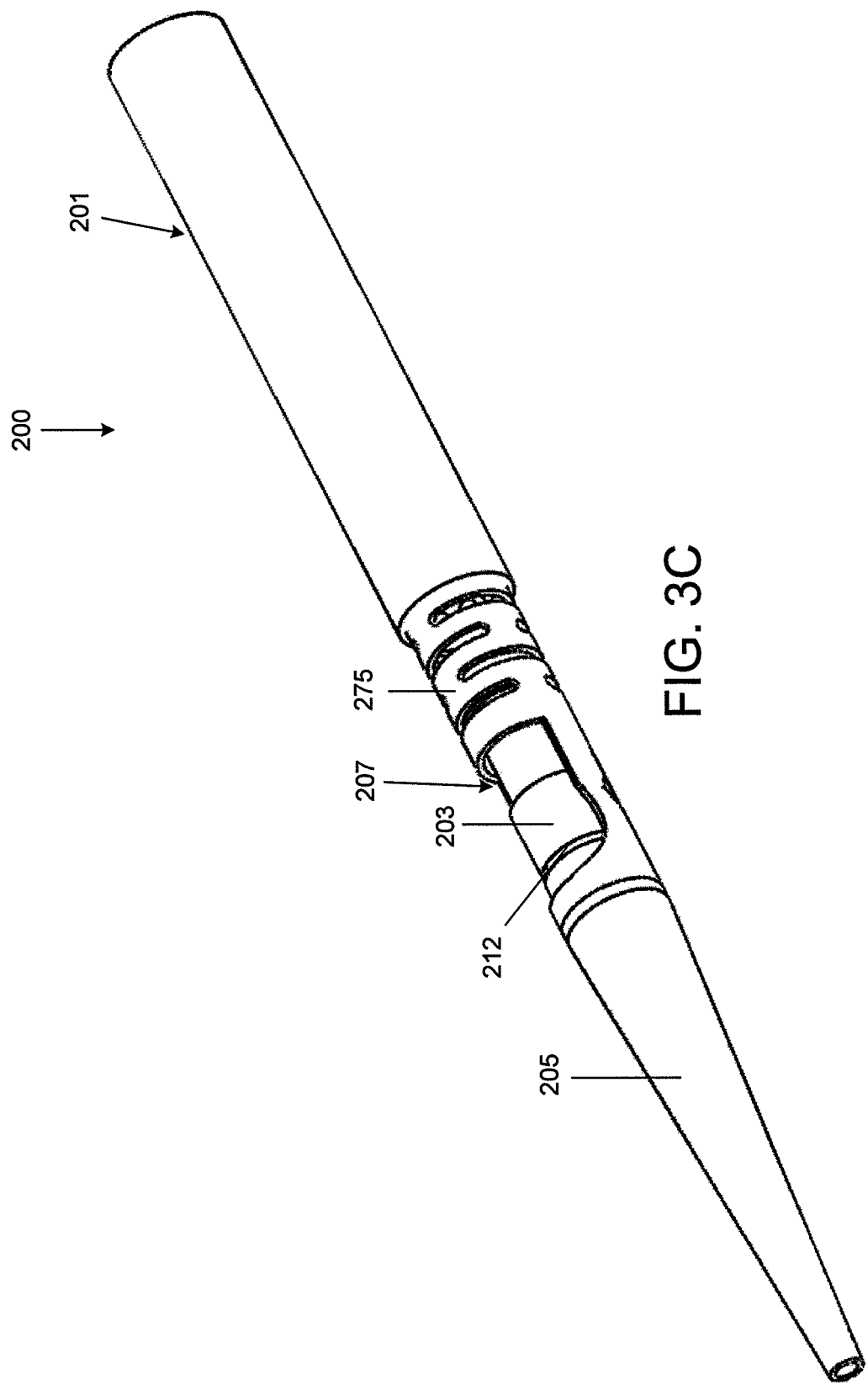

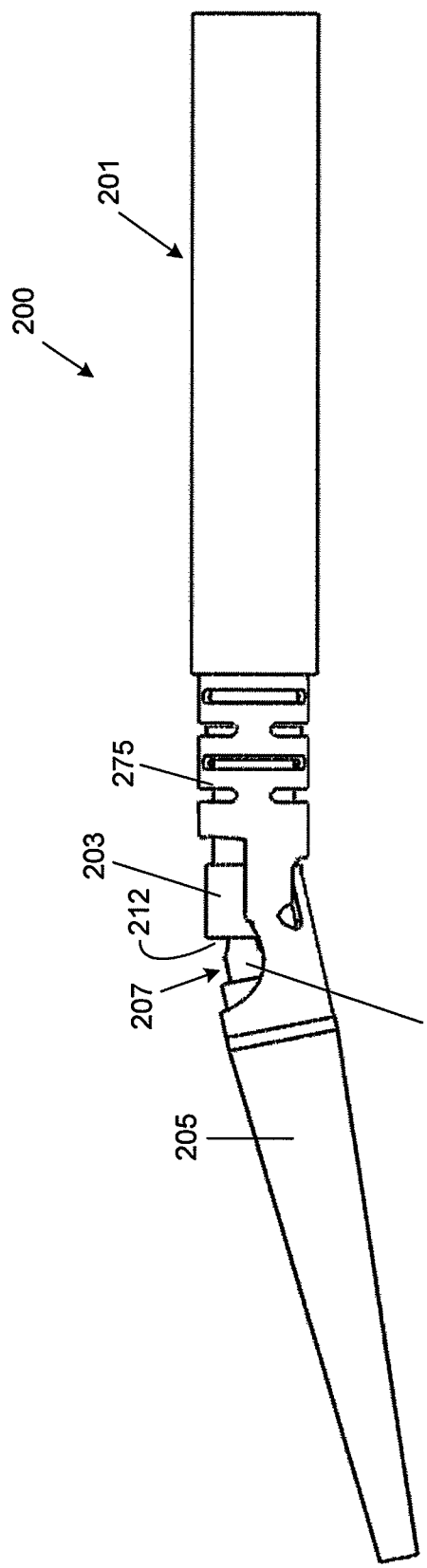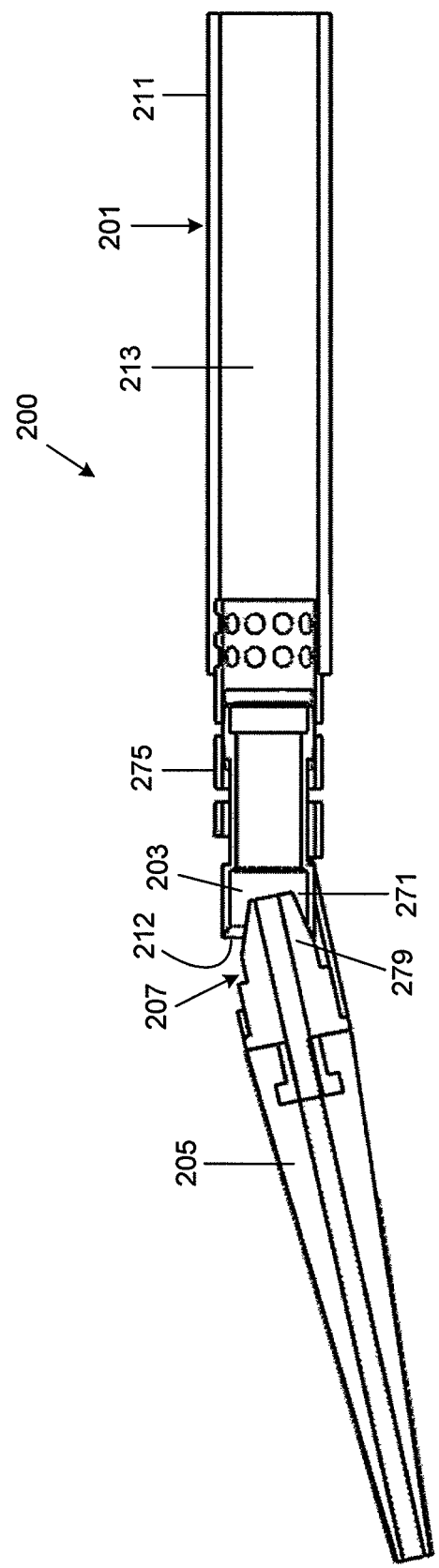
FIG. 3D
FIG. 3E

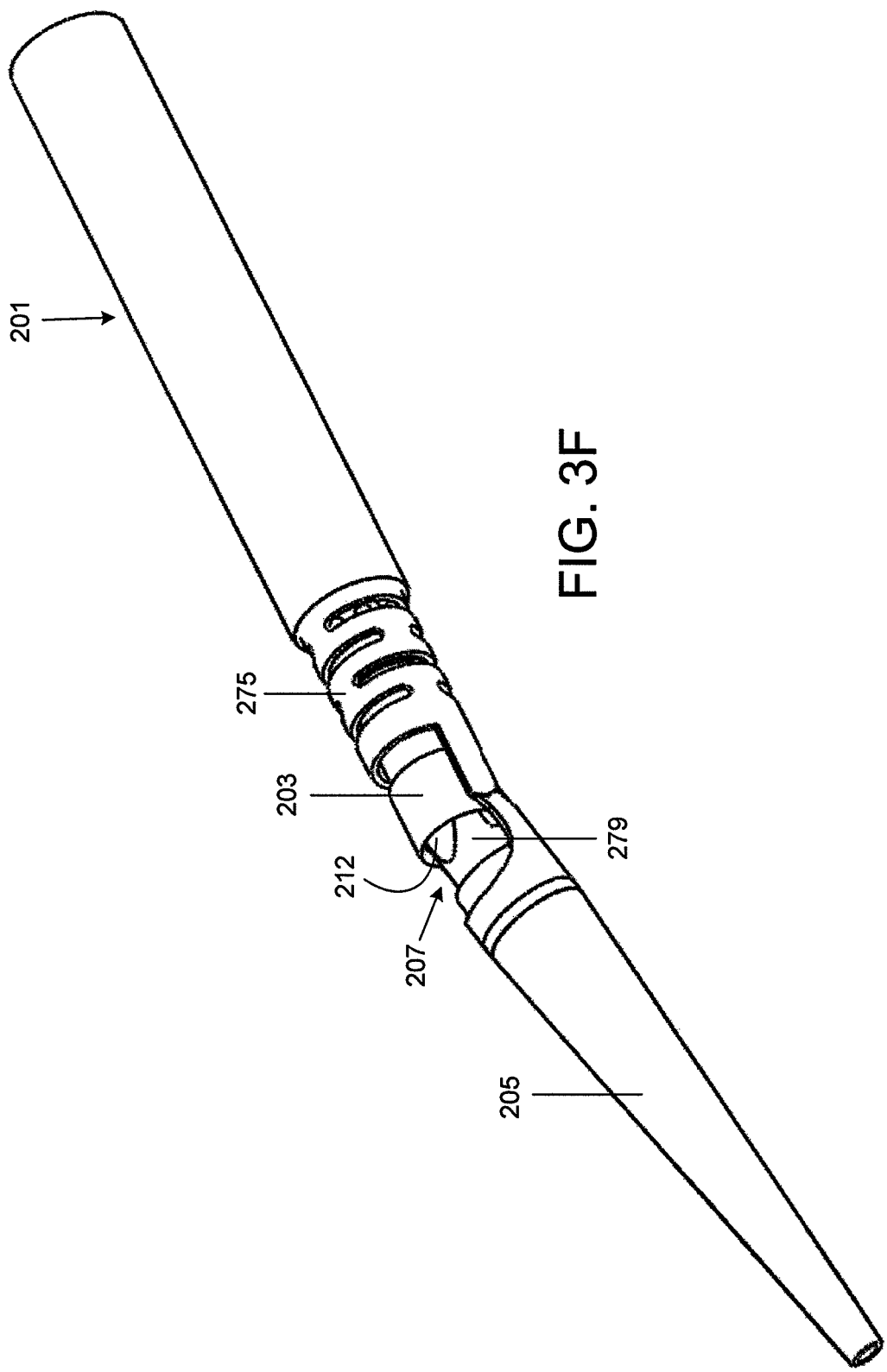

ATHERECTOMY CATHETERS WITH IMAGING

CROSS REFERENCE TO RELATED APPLICATIONS

This application is the U.S. National Stage Entry of International Patent Application No. PCT/US2013/031901, titled "ATHERECTOMY CATHETERS WITH IMAGING," filed on Mar. 15, 2013, which claims priority to U.S. Provisional Application No. 61/646,843, titled "ATHERECTOMY CATHETERS WITH IMAGING," filed on May 14, 2012, which applications are incorporated by reference in their entireties herein.

This application may be related to U.S. patent application Ser. No. 13/175,232, titled "ATHERECTOMY CATHETERS WITH LONGITUDINALLY DISPLACEABLE DRIVE SHAFTS," filed Jul. 1, 2011, Publication No. US-2012-0046679-A1, which is incorporated by reference herein in its entirety.

INCORPORATION BY REFERENCE

All publications and patent applications mentioned in this specification are herein incorporated by reference in their entireties to the same extent as if each individual publication or patent application was specifically and individually indicated to be incorporated by reference.

BACKGROUND

A significant body of scientific and clinical evidence supports atherectomy as a viable primary or adjunctive therapy prior to stenting for the treatment of occlusive arterial disease. Atherectomy offers a simple mechanical advantage over alternative therapies. By removing the majority of plaque mass (debulking), it creates a larger initial lumen and dramatically increases the compliance of the arterial wall. As a result, stent deployment is greatly enhanced.

Additionally, atherectomy provides several advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By using atherectomy to remove the disease with minimal force applied to the vessel, large gains in lumen size can be created with decreased vessel wall injury and limited elastic recoiling. These effects have been shown to generate better acute results and lower restenosis rates.

Despite its advantages, atherectomy is not commonly performed due to the cost, complexity and limited applicability of available atherectomy devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to a lack of intravascular visualization or requires very long procedure times. Based on these limitations, current devices are likely to perform poorly in the coronary vasculature where safety and efficacy in de novo lesions, ostials, and bifurcations continue to pose great challenges.

In the past, atherectomy devices have focused on macerating or emulsifying the atherosclerotic plaque such that either it might be considered clinically insignificant enough to remain in the blood stream or that it can be aspirated proximally through small spaces in the catheter main body. When the plaque is not aspirated through the catheter to an external reservoir, the reliability of these devices to produce clinically insignificant embolization has been challenged. Aspiration necessitates that a vacuum be applied to a lumen or annular space within the catheter to remove emulsified tissue. In early clinical evaluations of aspiration, the presence of negative pressure at the distal working assembly caused the artery to collapse around the cutting element. This effect results in more aggressive treatment, dissections and/or perforations. In addition, options for post-procedural analysis of any removed disease are extremely limited or impossible using this methodology.

Other atherectomy devices include directional atherectomy devices, which use cup-shaped cutters that cut and "turn" the tissue distally into a storage reservoir in the distal tip of the device. This approach preserves the "as cut" nature of the plaque, but requires large distal collection elements. These large distal tip assemblies can limit the capability of the system to access small lesions and may cause additional trauma to the vessel.

Currently available atherectomy devices also do not include, and are poorly adapted for use with, real time image guidance. Although intravascular diagnostic devices have consistently shown lesions that are significantly eccentric, the typical practice of physicians is to treat target lesions as if they contain concentric disease. This circumferential treatment approach virtually ensures that potentially native arterial wall and healthy vessel will be cut from the vasculature.

Further, several design challenges are presented by a single use, disposable, and single-direction imaging catheter, such as an atherectomy catheter. For example, obtaining a clear image can be difficult, as nonuniform rotational distortion ("NURD") can occur in the image as a result of the cutter vibrating or stalling as it encounters different types of tissue. Moreover, the imaging fiber, which runs from the static light source to the rotating distal tip, can become wound up as the catheter is in active (cutting) mode. Further, a motor can be required to drive the imaging assembly at the appropriate revolution rates for imaging, thereby significantly increasing the cost and complexity of the catheter.

Atherectomy catheter devices, systems and methods that may address some of these concerns are described and illustrated below.

SUMMARY OF THE DISCLOSURE

Described herein are various embodiments of atherectomy catheters.

In general, in one embodiment, an atherectomy catheter includes an elongate flexible catheter body, an elongate deflectable distal tip coupled to the catheter body at a hinge point, a rotatable cutter near the distal end of the catheter body and a drive shaft extending within the catheter body and configured to rotate the cutter. The atherectomy catheter further includes an optical fiber extending through the drive shaft substantially on-axis with the catheter body and attached to the cutter. The optical fiber is configured to rotate with the drive shaft. The atherectomy catheter further includes a wedge configured to deflect the distal tip away from the catheter body at the hinge point upon axial movement of the drive shaft.

This and other embodiments can include one or more of the following features. The hinge point can include a pin, and the wedge can be attached to the catheter body and the distal tip through the pin. The wedge can include a distally-facing annular flange configured to interact with a proximally-facing annular flange on the cutter to deflect the distal tip. The wedge can be configured such that proximal movement of the drive shaft causes the distal tip to deflect. The wedge can be configured such that distal movement of the drive shaft causes the distal tip to align axially with the catheter body. The drive shaft can be configured such that, after axial alignment of the distal tip with the catheter body, further distal movement of the drive shaft can move the cutter into the distal tip. The optical fiber can be coupled to the cutter but otherwise free to float within the drive shaft. The optical fiber can be configured to transmit an optical coherence tomography signal. Deflection of the distal tip away from the catheter at the hinge point can expose the cutter. When the distal tip is not deflected, it can be substantially on-axis with the elongate flexible catheter body. The rotatable cutter can be protected by the distal tip when the distal tip is substantially on-axis with the elongate flexible catheter body. The distal tip can include a cutter window therein. The cutter window can have a width that is greater than a diameter of the cutter. The cutter window can be asymmetric.

In general, in one embodiment, an atherectomy catheter includes an elongate flexible catheter body, a deflectable distal tip coupled to the elongate body, a rotatable cutter near the distal end of the catheter body and a living hinge configured to couple the catheter body and the distal tip. The living hinge is biased in an open configuration where the distal tip is deflected away from a central axis of the catheter body to expose the cutter. The atherectomy catheter further includes a drive shaft extending within the elongate flexible catheter body and configured to rotate the rotatable cutter. The atherectomy catheter further includes a wedge configured to hold the deflectable distal tip inline with the central axis of the catheter body.

This and other embodiments can include one or more of the following features. The atherectomy catheter can further include a drive shaft configured to rotate the rotatable cutter. The drive shaft can further be configured to move proximally and distally to engage or disengage the wedge from a matching notch. Proximal movement of the drive shaft can cause the wedge to disengage from the notch and the living hinge to bias the distal tip such that the distal tip is deflected away from the central axis of the catheter. Distal movement of the drive shaft can cause the wedge to engage the notch such that the distal tip is moved inline with the elongate catheter body. The drive shaft can be hollow and can be configured to hold cut tissue therein. The wedge can include a proximal extension from the nosecone. A distal face of the cutter can include a notch configured to mate with the proximal extension from the nosecone. The cutter can be hollow. The atherectomy catheter can further include an imaging element attached to the cutter. The imaging element can be an optical coherence tomography imaging element.

Stiffening Members

In general, in one embodiment, an atherectomy catheter includes an elongate catheter body having stiffening members therein, and a rotatable cutter having a distal cutting edge near the distal end of the elongate body. The atherectomy catheter further includes a drive shaft extending through the elongate catheter body and connected to a rotatable cutter. The drive shaft is configured such that axial movement of the drive shaft places compression on the elongate catheter body to cause the elongate catheter body to assume a predetermined shape defined by the placement of the stiffening members.

This and other embodiments can include one or more of the following features. A proximal end of the elongate body and a distal end of the elongate body can be offset but substantially parallel to one another. The atherectomy catheter can further include a nosecone attached to the elongate catheter body. In some embodiments, there is no hinge between the nosecone and the elongate body. The atherectomy catheter can further include a nosecone attached to the elongate body and a hinge between the nosecone and the elongate body configured, when hinged, to expose the cutter. The drive shaft can be configured such that proximal movement of the drive shaft can deflect the cutter and can activate the hinge to expose the cutter. The atherectomy catheter can further include an imaging element attached to the cutter. The imaging element can be an optical coherence tomography imaging element.

In general, in one embodiment, an atherectomy catheter includes an elongate shaft and a distal tip attached to the elongate shaft, the distal tip including a proximal-facing cutting edge configured to scrape tissue from a vessel wall.

This and other embodiments can include one or more of the following features. The distal tip can further include a distal-facing fluted cutting edge. The atherectomy catheter can further include an imaging element attached to the elongate shaft. The imaging element can be an optical coherence tomography imaging element.

In general, in one embodiment, an atherectomy catheter includes an elongate catheter body having a fixed jog therein. The fixed jog includes a distal inflection point and a proximal inflection point. The inflection points have opposite curvatures. The atherectomy catheter further includes a rotatable cutter having a distal cutting edge near the distal end of the elongate body. A distance from the distal cutting edge to the distal inflection point is less than a distance from the distal inflection point to the proximal inflection point.

This and other embodiments can include one or more of the following features. An angle of the distal inflection point can be between 120 and 180 degrees, and an angle of the proximal inflection point can be between 120 and 180 degrees. The angle of the distal inflection point can be 140 degrees and the angle of the proximal inflection point can be 160 degrees. The catheter can further include a nosecone attached to the elongate body and can have a cutting window therein configured to expose the cutter. The cutting window can be positioned along a same side of the elongate body as a convex portion of the distal inflection point. In one embodiment, there is no hinge between the nosecone and the elongate body. The atherectomy catheter can further include a hinge between the nosecone and the elongate body configured, when hinged, to expose the cutter. A proximal end of the elongate body and a distal end of the elongate body can be offset but substantially parallel to one another. The fixed jog can include pre-deflected shaped-set ribbon segments. The atherectomy catheter can further include an imaging element attached to the cutter. The imaging element can be an optical coherence tomography imaging element.

Methods of using these atherectomy devices are also described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A-3F show an atherectomy catheter having a living hinge mechanism and a nosecone wedge to open or close the nosecone. FIG. 3A is an outer view of the device with the nosecone closed. FIG. 3B is a cross-section of the device with the nosecone closed. FIG. 3C is an isometric view of the device with the nosecone closed. FIG. 3D is an outer view of the device with the nosecone open. FIG. 3E is a cross-section of the device with the nosecone open. FIG. 3F is an isometric view of the device with the nosecone open.

FIG. 4A shows a variety of different potential cuts for use as a living hinge. FIG. 4B shows the resulting deflection of one of the cuts of FIG. 4A.

DETAILED DESCRIPTION

Described herein are variations of atherectomy devices having imaging capabilities. In general, the atherectomy devices include an elongate flexible catheter body and an annular rotatable cutter configured to rotate to shear tissue away from the vessel wall. In other embodiments, rather than having an annular cutter, the atherectomy catheter can include a distal tip having a proximal-facing cutting edge configured to scrape tissue away from the vessel wall.

The atherectomy devices can further include on-board imaging, such as optical coherence tomography imaging. The optical fiber for the OCT imaging can, for example, extend substantially on-axis with the catheter body. In some embodiments, the optical fiber can be attached to the rotatable cutter and configured to rotate therewith. In other embodiments, the optical fiber can be attached to a separate imaging shaft.

In some embodiments, the atherectomy catheters described herein can include a nosecone that deflects to expose a cutter. The deflection can occur, for example, by pulling or pushing on a drive shaft to activate a wedge. The deflection can also occur through a pre-biased living hinge.

In some embodiments, the atherectomy catheters described herein can include a fixed or deflectable jog in the catheter configured to urge the cutter against the wall.

It should be understood that features of any of the embodiments described herein can be combined or replaced with features of other embodiments.

Figure 1:
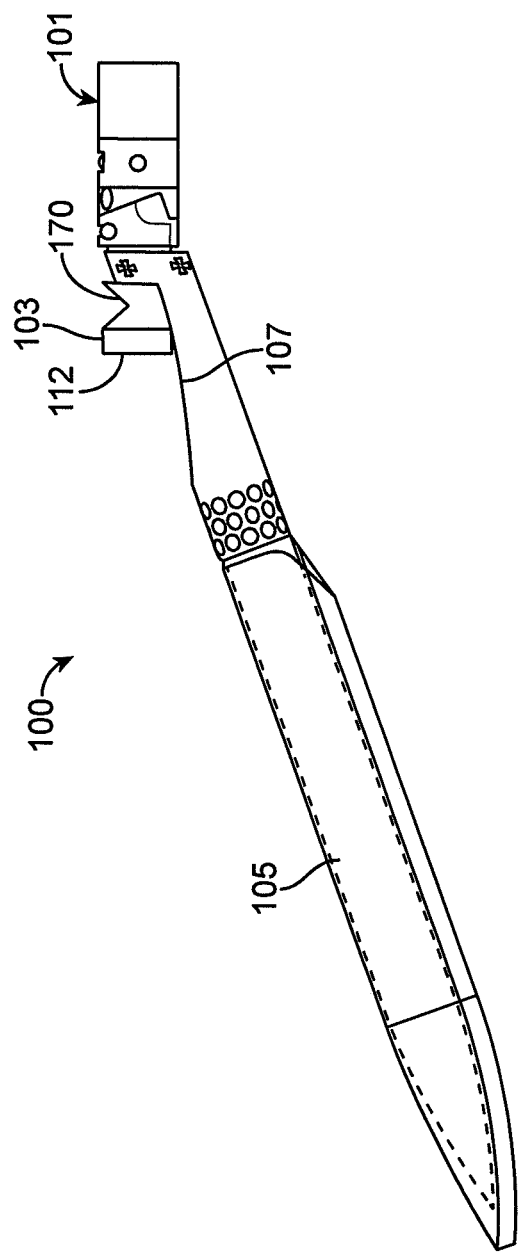
FIG. 1 shows a variation of a distal end of an atherectomy catheter that includes both cutting and imaging elements. This embodiment includes a hinged nosecone that is activated by tensioning the drive shaft to position the cutter and imaging element against a distal wedge through use of a distal wedge
Figure 2A:
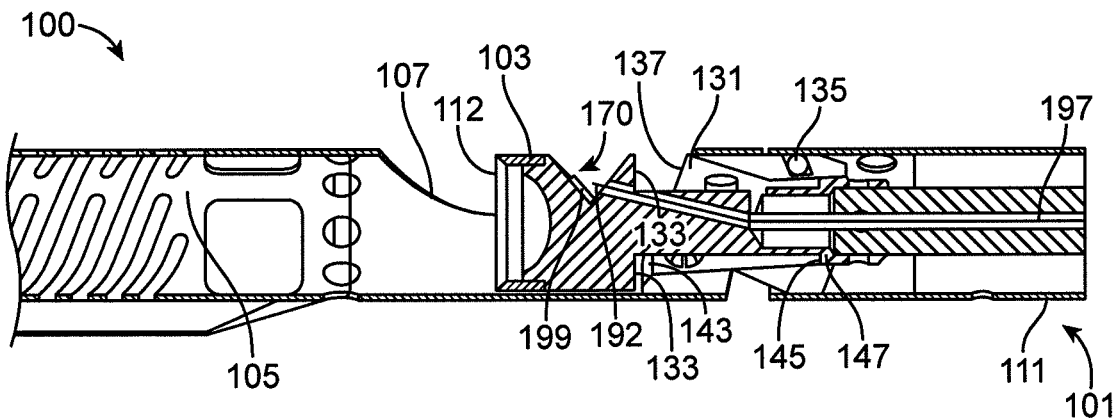
FIG. 2A shows a section view of a portion of the catheter of FIG. 1 with the nosecone in a closed position.
Figure 2B:
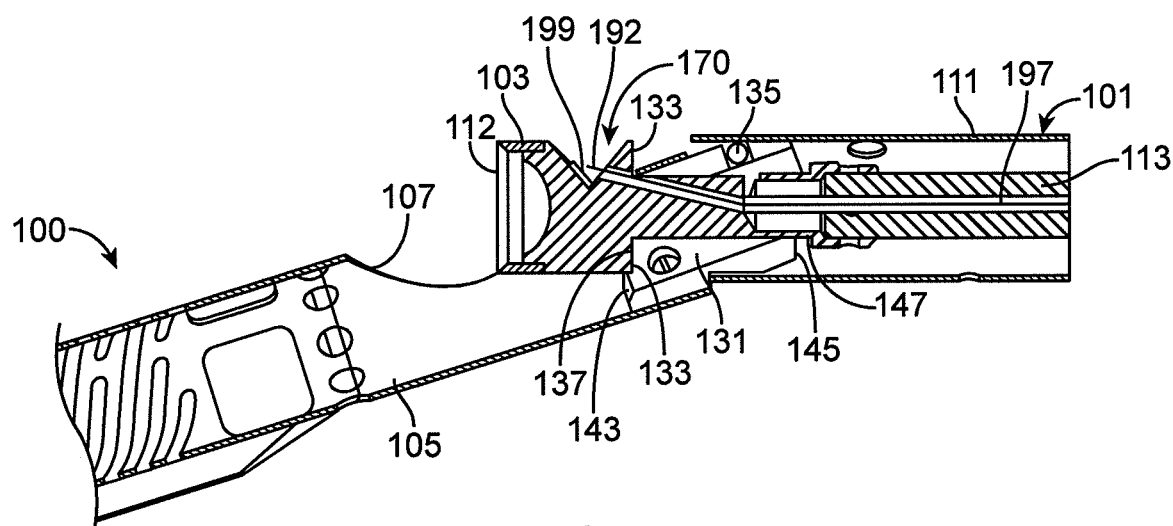
FIG. 2B shows a section view of a portion of the catheter of FIG. 1 with the nosecone in an open position.

FIGS. 1-2B show an example of an atherectomy catheter including a nosecone that deflects to expose a cutter. Referring to FIG. 1, an atherectomy catheter 100 can include a catheter body 101, a cutter 103 at a distal end of the catheter body 101, and a nosecone 105 at a distal end of the catheter body 101. The nosecone 105 can further include a cutting window 107 through which the cutting edge 112 of the cutter 103 can be exposed. The nosecone 105 can be configured to deflect away from the longitudinal axis of the catheter body at an angle, such as through a wedge. In use, this deflection can expose the cutter 103 through the cutting window 107 and/or radially push the cutter 103 into a wall of the vessel in which the atherectomy catheter is inserted.

Referring to FIGS. 2A-2B, the cutter 103 can be positioned between the catheter body 101 and the nosecone 105. A cutting window 107 in the nosecone can be configured to expose the cutter 103 therethrough. Thus, the cutting window 107 can have a width that is greater than the diameter of the cutter 103. In some embodiments, as shown in FIGS. 2A-2B, the cutter 103 can be an annular cutter with a sharp distal edge 112. The cutter 103 can be attached to a drive shaft 113 configured to rotate the cutter 103. Further, the catheter body 101 can include an outer shaft 111 outside of and concentric with the drive shaft 113.

Further, referring still to FIGS. 2A-2B, the atherectomy catheter 100 can include an imaging element 192, such as an OCT imaging element, proximal to the cutting edge 112 of the cutter 103. The imaging element 192 can include an optical fiber 197 that runs substantially on-axis through the center of the elongate body, such as through a drive shaft 113, to transmit the OCT signal. The optical fiber 197 can be attached at the distal end to the cutter 103, such as in a slot 170 in the cutter 103. The optical fiber 197 can otherwise be free to float within the catheter body or drive shaft 113. In other embodiments, the optical fiber 197 can be attached to the drive shaft 113 along the length thereof.

As shown in FIGS. 2A-2B, a reflective element 199, such as a mirror, can further be located within the slot 170 in the cutter 103 to radially direct light from the optical fiber 197 into the adjacent tissue (through the cutter window 107). The reflective element 199 can be oriented at an angle relative to the axis of the optical fiber 197, such as at a 35-55 degree angle, e.g. 45 degree angle, to reflect light into the tissue. The distal end of the optical fiber 197 can be located less than 3 mm from the cutting edge, such as less than 1.5 mm from the cutting edge, such as less than or equal to 1.2 mm, such as less than or equal to 1 mm. By having the imaging element 192 close to the cutting edge, the resulting image can advantageously align with the portions of the vessel being cut.

In use, the outer shaft 111 can be configured to be turned, such as turned manually, to position the cutter window 107, cutter 103 and/or the imaging element 192 toward the desired location. Rotation of the cutter can provide cutting due to the rotational motion of the cutting edge and provide the rotation necessary to image the vessel wall via the imaging element. The drive shaft can be rotated at up to 2,000 rpm, such as approximately 1,000 rpm in a single direction, though rotation in both directions or at higher or lower speeds is possible.

Referring to FIGS. 2A and 2B, the drive shaft 113 can further be configured to translate axially in the proximal and/or distal directions. Such axial movement of the drive shaft 113 can open and/or close the nosecone 105 to expose or conceal and protect the cutting edge 112 of the cutter 103. For example, as shown in FIGS. 2A-2B, the cutter can include an annular wedge 131 that is attached to the outer shaft 111 (or a distal housing around the outer shaft) and nosecone 105 through a pin 135. The wedge 131 can include a distally-facing annular flange that includes a lower lip 143 and an upper slanted surface 137. Further, the cutter 103 can include a proximally-facing annular flange 133. As described further below, the interaction between these two flanges 137/143 and 133 can cause the nosecone 105 to open. Further, the wedge 131 can include a proximally-facing annular flange 145 while the cutter 103 can include a distally-facing annular flange 145. As described below, the interaction between these two flanges 145, 147 can cause the nosecone 105 to close.

Thus, in one embodiment, proximal retraction of the drive shaft 113 opens the nosecone 105 to expose the cutter. For example, as shown in FIG. 2A, when the drive shaft 113 is translated proximally, the cutter 103 can retract proximally until it contacts the wedge 131 that is attached to the outer shaft 111 and nosecone 105 through a pin 135. As the cutter flange 133 pushes on the lip 143 of the wedge flange, the lip 143 will rotate downward, causing the wedge 131 to pivot away from the outer shaft 111, rotating about the axis of the pin 135. The rotation of the wedge 131 about the pin 135 will likewise cause the nosecone 105 to rotate, thereby dropping the nosecone away from the central axis and exposing the cutting edge 112, as shown in FIG. 2B. The cutting window 107 can have an opening that is larger than the diameter of the cutter 103 and cutting edge 112 to allow the cutter 103 to protrude out of the nosecone 105. As shown in FIG. 2B, when the nosecone 105 is in the fully open position, the cutter fits snugly against the inner surface of the lip 143 while the slanted surface 137 and the cutter flange 133 will rest against one another in a coplanar position that is approximately perpendicular to the central axis of the elongate body.

In one embodiment, distal movement of the drive shaft 113 closes the nosecone 105. For example, as shown in FIG. 2B, when the drive shaft 113 is pushed distally, the flange 147 on the cutter will hit the flange 145 on the wedge. As a result, the flange 145 will be pushed distally, causing the wedge 131 to rotate up about the pin 135, thereby causing the nosecone 105 to also rotate upwards back into alignment with the elongate body, as shown in FIG. 2A. The return of the nosecone 105 to the closed position can also be aided by having a tight concentric fit between a proximal end of the nosecone 105 and the outer shaft 111 such that once the proximal end of the nosecone 105 begins to align with outer shaft 100, it is forced upwards and into alignment. A handle can be used to control the rotation or translation of the driveshaft. Exemplary handles are described in co-pending patent applications: U.S. patent application Ser. No. 13/654, 357, titled "ATHERECTOMY CATHETERS AND NON-CONTACT ACTUATION MECHANISM FOR CATHETERS," filed Oct. 17, 2012; International Patent Application titled "BALLOON ATHERECTOMY CATHETERS WITH IMAGING," filed herewith; U.S. patent application Ser. No. 12/829,277, titled "ATHERECTOMY CATHETER WITH LATERALLY-DISPLACEABLE TIP," filed Jul. 1, 2010, Publication No. US-2011-0004107-A1; U.S. patent application Ser. No. 13/175,232, titled "ATHERECTOMY CATHETERS WITH LONGITUDINALLY DISPLACEABLE DRIVE SHAFTS," filed Jul. 1, 2011, Publication No. US-2012-0046679-A1; U.S. patent application Ser. No. 13/675,867, titled "OCCLUSION-CROSSING DEVICES, ATHERECTOMY DEVICES, AND IMAGING," filed Nov. 13, 2012, the entireties of which are incorporated by reference herein.

Further, the atherectomy catheter 100 can include a mechanism for packing tissue into the nosecone, such as by moving the drive shaft axially. In one embodiment, movement of the drive shaft 113 distally closes the nosecone 105. Moving the drive shaft 113 further distally will move the cutter 103 into the nosecone 105, thus packing tissue with a distal face of the cutter 103. In some embodiments, the housing window 107 can be asymmetric to avoid having the cutter crash into the edge of the cutter window 107, as described further in International Patent Application titled "BALLOON ATHERECTOMY CATHETERS WITH IMAGING," filed herewith, the entirety of which is incorporated herein by reference.

In one embodiment, the atherectomy catheter 100 includes a guidewire lumen in the nosecone 105, such as a monorail, for use in guiding the catheter. Advantageously, the guidewire lumen can be used as a marker during imaging.

In one embodiment, the atherectomy catheter 100 includes a flush port close to the cutter 103. The plush port can be used to deliver flushing fluid to the region of imaging, thereby improving image quality. In some embodiments, the flushing can be activated through a mechanism on the handle of the device.

FIGS. 3A-3F show another exemplary atherectomy catheter 200 that includes a nosecone that deflects to expose a cutter. The atherectomy catheter 200 can include a catheter body 201, a cutter 203 at a distal end of the catheter body 201, and a nosecone 205 at a distal end of the catheter body 203. The nosecone 205 (or a distal housing connecting the nosecone 205 and catheter body 201) can further include a cutting window 207 through which the cutting edge 212 of the cutter 203 can be exposed. As shown in FIGS. 3D-3F, the nosecone 205 can be configured to deflect away from the longitudinal axis of the catheter body 201 at an angle, such as through a living hinge mechanism. In use, this deflection can expose the cutter 203 through the cutting window 207 and/or radially push the cutter 203 into a wall of the vessel in which the atherectomy catheter 200 is inserted by deflecting the nosecone 205 against the opposite vessel wall.

Referring to FIGS. 3D-3F, the cutter 203 can be positioned between the catheter body 201 and the nosecone 205. The cutting window 207 can be configured to expose the cutter 203 therethrough. Thus, the cutting window 207 can have a width that is greater than the diameter of the cutter 203. In some embodiments, as shown in FIGS. 3A-3F, the cutter 203 can be an annular cutter with a sharp distal edge 212. The cutter 203 can be attached to a drive shaft 213 configured to rotate the cutter 203. Further, the catheter body 201 can include an outer shaft 211 outside of and concentric with the drive shaft 213.

As shown in FIGS. 3C and 3F, the cutter 203 and drive shaft 213 can be hollow, thereby providing a collection chamber or feed-through channel for tissue cut during the atherectomy procedure. Advantageously, by feeding tissue into the hollow drive shaft 213 rather than the nosecone, the nosecone 205 can be shorter, such as less than 1" or less than 0.5". By having a shorter nosecone, the distance that the atherectomy catheter has to travel through the diseased or occluded vessel before cutting is advantageously decreased.

In some embodiments, a wedged geometry (which can be a sloped surface or any other feature that mechanically interlocks with a mating feature) in the nosecone can be used to control the opening and closing of the nosecone 205. Further, in some embodiments, the catheter 200 can include a shape memory living hinge mechanism 275 configured to bias the nosecone open or close.

For example, as shown in FIGS. 3A-3F, the cutter 203 can include a notch 271 in the distal end thereof (which can extend all the way through the cutter to make the cutter hollow, as described above). Further, the nosecone 205 can include a wedge 279 extending therefrom and configured to mate within the notch 271 in the cutter 203. Moreover, a living hinge mechanism 275 can extend between the catheter body 201 and the nosecone 205. The living hinge mechanism 275 can be a single piece of material, such as a single piece of shape-memory alloy, such as nickel titanium (e.g., nitinol). Cuts 277 (labeled in FIG. 3A) in the living hinge mechanism 275 can ensure that the nosecone opens is such a way as to expose the cutter. The living hinge mechanism 275 can be biased in an open configuration (such as the configuration shown in FIGS. 3C-3F). Further, a proximally-extending tongue 251 in the living hinge mechanism 275 can be configured to limit the amount of deflection that the nosecone 205 can undergo.

To open the nosecone 205, the drive shaft 213 can be pulled proximally, thereby pulling the cutter 203 proximally. By doing so, the notch 271 of the cutter 203 can disengage from the wedge 279 of the nosecone. Because the hinge mechanism 275 is biased to an open configuration, releasing the wedge 270 from the notch 271 will cause the nosecone 205 to deflect away from the catheter body 201, thereby exposing the cutting edge 212 of the cutter 203 through the cutting window 207.

To close the nosecone, the drive shaft 213 can be pushed distally. Pushing distally can cause the notch 271 of the cutter 203 to reengage with the wedge 279, forcing the wedge 279 back into alignment with the cutter 203 and therefore the catheter body 201. This mechanism of closing can also shear tissue from the vessel that is stuck between the wedge 279 and the notch 271, thereby fully completing the cut.

Figure 4A:
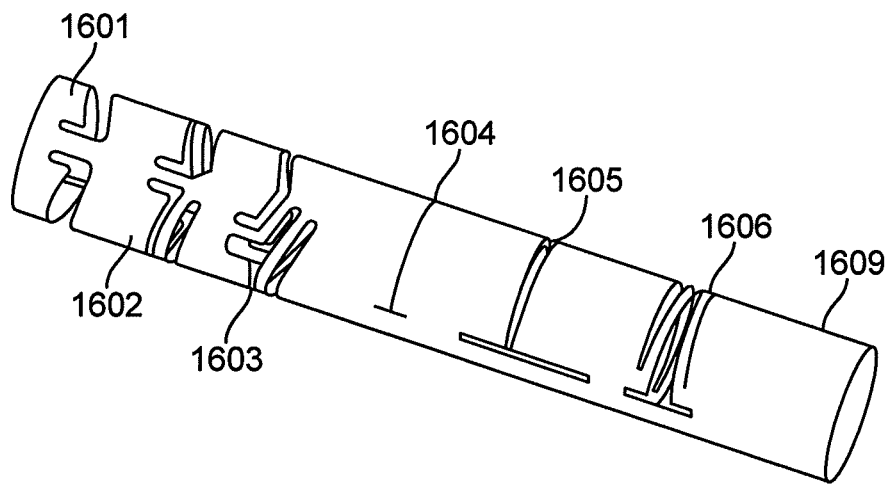
FIGS. 4A-4B show various embodiments of a living hinge.
Figure 4B:
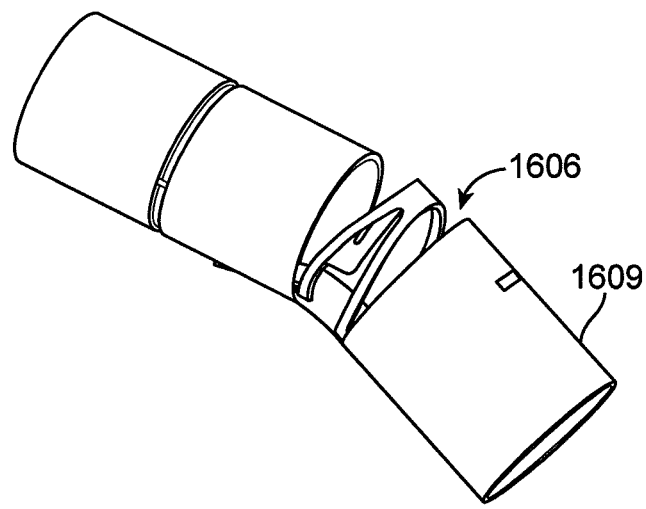

Referring to FIGS. 4A-4B, alternate living hinge mechanisms are possible. In general, the living hinge mechanism can include cuts in the tube that are configured to ensure that the hinge pivots in the proper orientation and is biased in the open configuration.

As shown in FIG. 4A, a living hinge can include one or more of a variety of different types of cuts to provide deflection in a tube 1609, such as cuts 1604, 1605, and 1606. Such deflecting cuts 1604, 1605, 1606 can be primarily on one side of the tube so as to leave a stemmed hinged portion on the opposite side of the tube. For example, the deflection of cut 1606 is shown in FIG. 4B. In some embodiments, rather than using the cut pattern to deflect the device, the cut pattern be used to return bias the nosecone back in line with the device, such as cuts 1601, 1602, and 1603. Such return bias cuts 1601, 16502, 1603 can include notches on both sides of the tube configured to provide both a hinge point and a return bias.

The atherectomy catheter 200 can further advantageously include a guidewire lumen 254 extending through the nosecone 205. A guidewire can thus be inserted through the hollow drive shaft 213, through the hollow cutter 203, and through the guidewire lumen 213. In an alternative embodiment, the guidewire lumen could be limited to the length of the nosecone 205, such as a monorail, for use in guiding the catheter. Advantageously, the guidewire lumen can be used as a marker during imaging.

Similar to the atherectomy catheter 100, the atherectomy catheter 200 can further include an imaging element, such as an OCT imaging element. In some embodiments, the optical fiber for the OCT imaging element can be attached to the outside of the drive shaft 213 to spin therewith. In other embodiments, a separate imaging shaft can be placed around the drive shaft 213 to hold the optical fiber 213. Further, the direction and speed of rotation, flush port, and other features described with respect to catheter 100 can further be incorporated into catheter 200.

In some embodiments, the atherectomy catheters described herein can include a jog in the catheter body that urges the atherectomy cutter against the vessel wall.

Figure 5A:
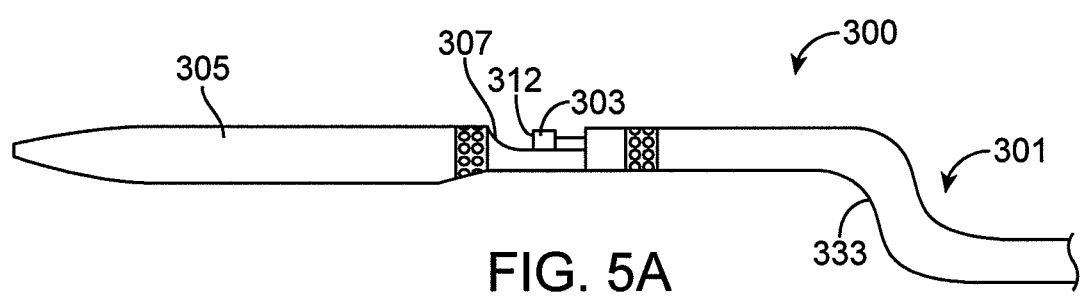
FIG. 5A shows a variation of a distal end of an atherectomy catheter that includes both cutting and imaging elements. This embodiment includes a mechanism to deflect the cutter out of a window and utilizes a fixed jog in the catheter outer shaft.
Figure 5B:
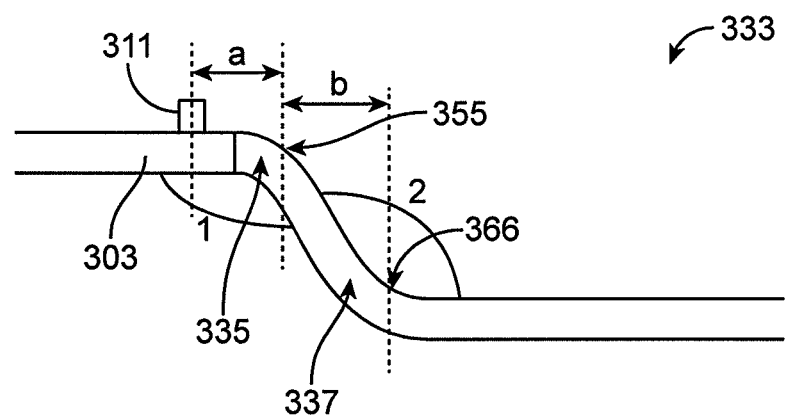
FIG. 5B is a schematic showing the dimensions and angles of the fixed jog.
Figure 6:
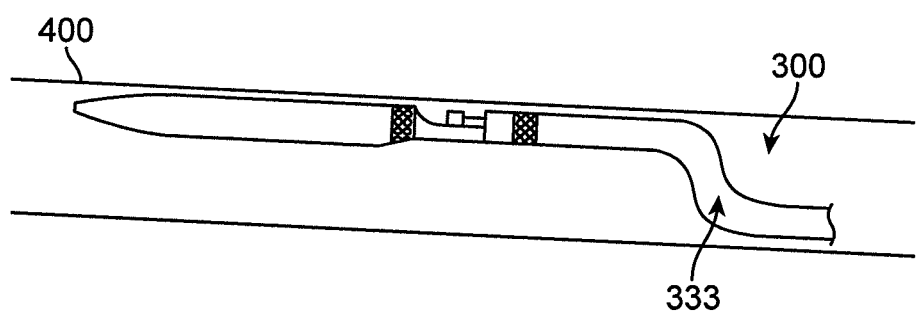
FIG. 6 shows placement of the atherectomy device of FIG. 5A in a vessel.

FIGS. 5A-6 show an exemplary catheter 300 that include a jog in the catheter body that urges the atherectomy cutter against the vessel wall. Referring to FIGS. 5A and 5B, an atherectomy catheter 300 can include a catheter body 301, a cutter 303 at a distal end of the catheter body 301, and a nosecone 305 at a distal end of the catheter body 301. The nosecone 305 can include a cutting window 307 configured to allow the cutter 303 to cut therethrough. The catheter 301 can further include a fixed jog 333 in the catheter body 301 to radially push the cutter 303 against the vessel wall.

As shown in FIGS. 5A and 5B, the fixed jog 333 can be configured such that the cutting window 307 is on the outermost portion of the jog 333 (thereby allowing the cutting window 307 to be urged against a vessel wall in use). In one embodiment, the fixed jog 333 can be formed, for example, by pre-deflected shaped-set nitinol ribbon segments embedded in the outer shaft. The fixed jog 333 can have two inflection points 355, 366 of opposite curvature (i.e., one curving up and the other curving down) so as to form an approximate "s" shape. In one embodiment, the s-shape can be configured such that a distal end of the catheter body 301 is offset from, but substantially parallel to, a proximal end of the catheter body 301. In other embodiments, the distal end and proximal ends of the catheter body 301 can be at a slight angle to one another so as to control the angle of cutter engagement with the vessel wall.

Thus, as shown in FIG. 5B, the "s-shaped" of the fixed jog 333 can have an angled section 337 that includes the inflection points of the jog. The angled section 337 can have a length b that extends from the distal end of the inflection point 355 to the proximal inflection point 366. Further, the fixed jog 333 can include a cutter section 335 having a length a that extends from the cutting edge 312 to the distal inflection point 355. Further, there can be distal angle 1 at the distal end of the "s-shape" and a proximal angle 2 at the proximal end of the "s-shape." These lengths (a, b) and angles (1, 2) can be tuned to achieve the desired jog or offset in order to obtain optimum apposition to tissue walls. For example, the length a can be shorter than the length b to ensure that the cutter is as close to the angle 1 as possible, thereby providing better apposition of the cutter. The angles 1 and 2 can be between 120 and 180 degrees, such as between 140 and 160 degrees. In one example, the length a is between 5 and 10 mm, the length b is between 10 and 15 mm, the angle 1 is 140 degrees and angle 2 is 160 degrees for a catheter configured to be used in a vessel having a 2.5-4 mm diameter. In an alternative embodiment, rather than having a fixed angle 1, a flexible section can be created in the catheter just proximal to the cutter such that, once the angle 2 deflects the catheter to approximately the appropriate position, the flexible section can bend to align the cutter with the edge of the vessel.

Referring to FIG. 6, the fixed jog 333 can advantageously radially push the distal end of the catheter against a vessel wall 400, thereby enabling optimized cutting and/or imaging of the vessel. The fixed jog 333 can advantageously be used alone or in combination with a mechanism to deflect the nosecone (such as described above with respect to catheters 100 and 200). If used alone, the cutting window 307 can be optimized so as to allow for automatic invagination of tissue into the cutting window 307. Having the nosecone 305 not deflect can advantageously prevent the cutter 303 from escaping from the nosecone 305 during packing. Further, having the fixed jog 333 can advantageously eliminate having to use additional mechanisms to force a jog mid-surgery, such as pulling or pushing on a shaft, thereby enhancing both ease of use and enhancing image stability.

Some or all of the type of cutter, imaging element configuration, packing of tissue, guidewire, and flush port of catheter 100 can likewise be incorporated into catheter 300.

Figure 7A:
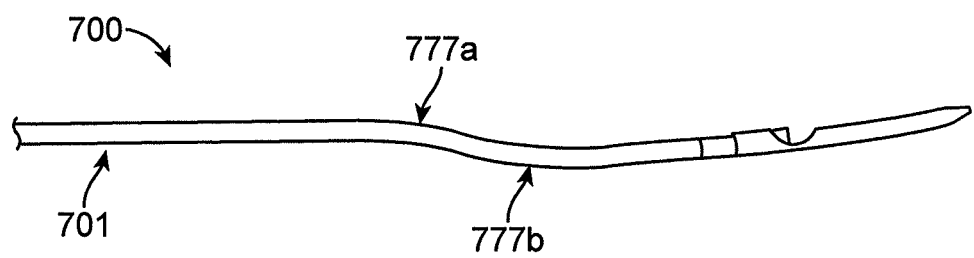
FIG. 7A shows a variation of a distal end of an atherectomy catheter that includes stiffening members that cause the catheter to deform to a predetermined configuration when activated.
Figure 7B:
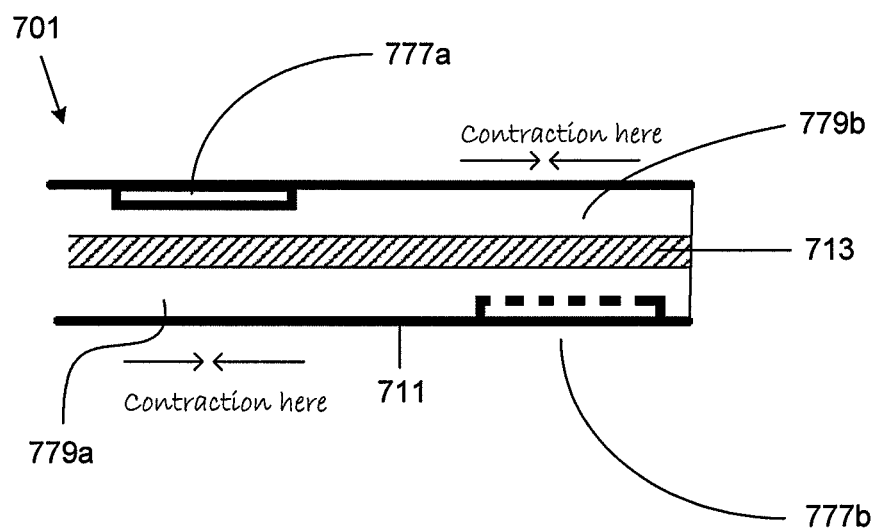
FIG. 7B is a schematic showing the stiffening members of FIG. 7A.

FIGS. 7A-7B show an exemplary catheter 700 that include a jog in the catheter body that urges the atherectomy cutter against the vessel wall.

Referring to FIGS. 7A and 7B, in some embodiments, a catheter 700, can be deflected into a jog 733 by tensile and compressive interaction between an inner shaft 713 (which can be a drive shaft for a cutter) and outer shaft 711 that are fixed together at the distal end but free to move relative to one another at the proximal end. The outer shaft 711 can include stiffening members 777a,b, such as nitinol or stainless steel, stiffening members, configured to bias the deflection to a set shape. As shown in FIG. 7B, there can be two stiffening members 777a, 777b that can be axially aligned with the outer shaft 711 and axially and radially offset from one another. As a result, when compression is applied on the outer shaft 711 (such as by pulling on the inner shaft 713), the portions 779a,b of the outer shaft opposite to the stiffening members 777a,b will contract. The contraction of the two portions 779a, 779b will result in an s-shape similar to the catheter 300 shown in FIG. 6. As a result, the catheter will deflect into jog or s-shaped configuration where the distal end of the shaft is offset and parallel to the main shaft body. It is to be understood that other numbers and arrangements of stiffening members are possible, as are other resulting jog shapes.

Similar to the fixed jog of the catheter 300, the jog mechanism of catheter 700 can be combined with a mechanism to deflect the nosecone (such as described above with respect to catheters 100 and 200). If used in combination, placing a first amount of tension on the drive shaft may deflect the cutter, as described with respect to catheter 100. Placing further tension on the drive shaft can cause the cutter to engage the distal end of the outer shaft, resulting in compression being applied to the outer shaft. Such compression can cause the outer shaft to assume a predetermined shape. Moreover, the jog mechanism of catheter 700 can be used with any of the other features of the catheters described herein (such as OCT imaging, rotating cutters, etc.).

Figure 8A:
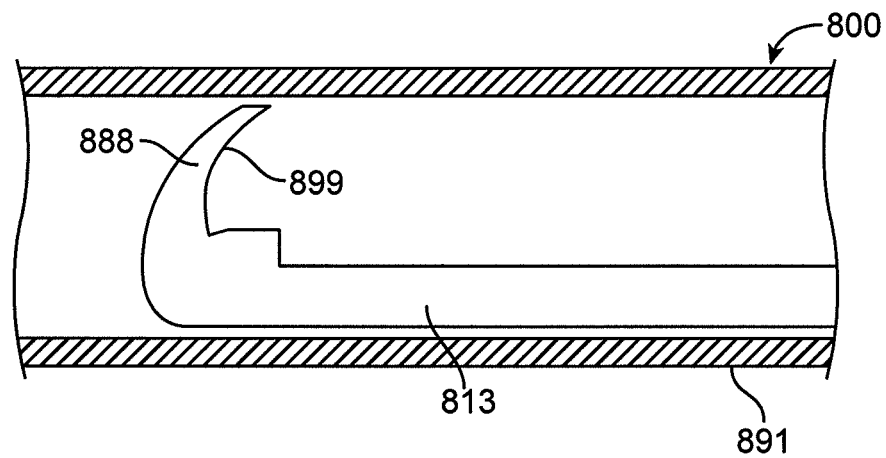
FIG. 8A shows a variation of a distal end of a catheter with both cutting and imaging elements. This embodiment includes a sharp directional blade configured to scrape tissue away from edges of a vessel wall.
Figure 8B:
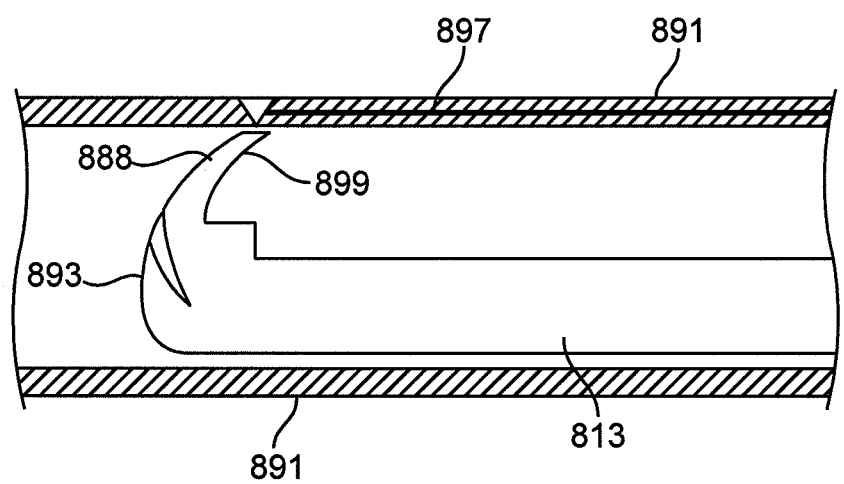
FIG. 8B shows the imaging components of the catheter of FIG. 8A.

In some embodiments, an atherectomy catheter can include a sharp blade on the distal end thereof. For example, referring to FIGS. 8A and 8B, in one embodiment, a catheter 800 can include a distal tip 888 having a cutting edge 891, such as a sharp blade, thereon. The distal tip 888 can be attached to a shaft 813. As shown in FIGS. 8A and 8B, the cutting edge 899 can be directional, e.g., can face in a proximal direction. The cutting edge 899 can be activated by pulling proximally on the shaft 813. In use in a vessel, when a proximal force is placed on the shaft 813, the cutting edge 899 can be pulled proximally and scrape, cut, or shave tissue from the inner walls of the vessel.

In some embodiments, the cutting edge 899 can be further activated ultrasonically or with an oscillating motor or cam system to create slight vibrations in the cutter, thereby assisting the cutting as the blade 888 is pulled proximally. The catheter 800 can include a retractable sheath 891 that can be configured to cover and shield the cutting edge 899 until the cutting edge 899 has reached the desired location to prevent inadvertent cutting of nontargeted tissue.

As shown in FIG. 8B, the distal tip 888 of the catheter 800 can include a distal drilling mechanism, such as a helical fluted cutting edge 893 on the distal surface of the tip 888. Further, the distal blade 888 can be configured to rotate, such as with the shaft 813. Having a rotatable fluted distal end can advantageously be used to cross chronic total occlusions (CTOs) and gain access to completely blocked vessels.

In use, the cutting edge 899 and/or distal fluted cutting edge 893 can remain covered by the retractable sheath 891. Once the catheter 800 is through the lesion, the retractable sheath 891 can be pulled back to expose the cutting edge 899 of the distal tip 888 to cut tissue. The device can then be pulled proximally across the lesion, cutting the targeted lesion as it is withdrawn. In embodiments (such as shown in FIG. 8B) where a distal cutting edge 893 is included, the distal cutting edge 893 can be rotated to help drill through the occlusion in one direction, followed by scraping of the material in the opposite direction.

As further shown in FIG. 8B, the catheter 800 can further include imaging, such as an optical fiber 897 for OCT. The imaging element can be present on the outer sheath 891, which can turn with the distal tip 888 during CTO crossing to provide radial imaging. After the catheter 800 is through the CTO, the sheath 891 can be pulled back slightly to expose the cutting edge 891. In some embodiments, the optical fiber 897 can remain rotationally stable (i.e. not be rotated). In these embodiments, as the cutter/sheath assembly is pulled proximally, the imaging element 891 can detect a linear view of the tissue being cut. In other embodiments, the outer sheath 891, and thus the optical fiber 897, can be rotated so as to obtain a 360 degree view of the vessel.

The catheters described herein can be driven using a drive assembly. Exemplary drive assemblies are described in co-pending patent applications: International Patent Application titled "ATHERECTOMY CATHETER DRIVE ASSEMBLIES," filed herewith and U.S. patent application Ser. No. 13/654,357, titled "ATHERECTOMY CATHETERS AND NON-CONTACT ACTUATION MECHANISM FOR CATHETERS," filed Oct. 17, 2012; both of which are incorporated by reference in their entireties.

Further, as described above, the catheters described herein can be configured to provide imaging, such as optical coherence tomography imaging. Exemplary imaging systems are described in co-pending applications: U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; International Patent Application titled "OPTICAL COHERENCE TOMOGRAPHY WITH GRADED INDEX FIBER FOR BIOLOGICAL IMAGING," filed herewith, all of which are incorporated by reference in their entireties. Further, although many of the embodiments described herein were described as having the optical fiber attached to the cutter, other variations are possible. For example, the optical fiber can be attached to a separate imaging shaft extending concentric to or parallel with the drive shaft, as described in International Patent Application titled "BALLOON ATHERECTOMY CATHETERS WITH IMAGING," filed herewith, which is incorporated herein by reference.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An atherectomy catheter comprising:
an elongate flexible catheter body extending from a proximal end to a distal end;
an elongate deflectable distal tip pivotally coupled to the catheter body;
a rotatable cutter near the distal end of the catheter body;
a drive shaft extending within the catheter body and configured to rotate the cutter;
an optical fiber extending through the drive shaft approximately on-axis with the catheter body, a distal end of the optical fiber attached to a slot in the cutter and a central portion of the optical fiber free to float within the drive shaft, the distal end of the optical fiber configured to rotate with the drive shaft; and
a hinge assembly that pivotally couples the distal tip to the catheter body the hinge assembly including a pin and a wedge, wherein proximal axial movement of the drive shaft causes the rotatable cutter to engage with a distally-facing surface of the wedge to rotate the distal tip about the pin away from the catheter body, wherein distal axial movement of the drive shaft causes the rotatable cutter to engage with a proximally-facing surface of the wedge to rotate the distal tip about the pin to align axially with the catheter body;

further wherein the drive shaft is configured such that, after axial alignment of the distal tip with the catheter body, further distal movement of the drive shaft moves the cutter into the distal tip to pack tissue into the distal tip.

2. The atherectomy catheter of claim 1, wherein the wedge is attached to the catheter body and the distal tip through the pin.

3. The atherectomy catheter of claim 1, wherein the distally-facing surface is on an annular flange of the wedge that is configured to interact with a proximally-facing annular flange on the cutter to deflect the distal tip.

4. The atherectomy catheter of claim 1, wherein the optical fiber is configured to transmit an optical coherence tomography signal.

5. The atherectomy catheter of claim 1, wherein deflection of the distal tip away from the catheter body at the hinge assembly exposes the cutter.

6. The atherectomy catheter of claim 1, wherein, when the distal tip is not deflected, the distal tip is approximately on-axis with the elongate flexible catheter body.

7. The atherectomy catheter of claim 1, wherein the rotatable cutter is protected by the distal tip when the distal tip is approximately on-axis with the elongate flexible catheter body.

8. The atherectomy catheter of claim 1, wherein the distal tip includes a cutter window therein.

9. The atherectomy catheter of claim 8, wherein the cutter window is asymmetric.

10. The atherectomy catheter of claim 1, further comprising first and second stiffening members within the elongate flexible catheter body and aligned with a longitudinal axis of the elongate flexible catheter body, the first stiffening member axially and radially offset from the second stiffening member, and wherein the drive shaft is configured such that axial movement of the drive shaft compresses portions of the elongate flexible catheter body surrounding the first and second stiffening members to cause the elongate flexible catheter body to assume a predetermined curved shape.

11. The atherectomy catheter of claim 1, wherein the proximally-facing surface is on an annular flange of the wedge that is configured to interact with a distally-facing annular flange on the cutter to axially align the distal tip with the catheter body.

12. An atherectomy catheter comprising:

an elongate catheter body having a distal end and a main shaft, the main shaft having first and second stiffening members therein that are aligned with a longitudinal axis of the main shaft, the first stiffening member axially and radially offset from the second stiffening member;

a rotatable cutter having a distal cutting edge near the distal end of the elongate catheter body, the rotatable cutter configured to retract within and extend through a cutting window of the catheter body; and a drive shaft extending through the elongate catheter body and connected to the rotatable cutter, wherein the drive shaft is configured such that axial movement of the drive shaft compresses portions of the elongate catheter body surrounding the first and second stiffening members to cause the main shaft to assume a predetermined s-shape when the rotatable cutter is retracted within the cutting window.

13. The atherectomy catheter of claim 12, further comprising a nosecone attached to the elongate catheter body, wherein there is no hinge between the nosecone and the elongate catheter body.

14. The atherectomy catheter of claim 12, further comprising a nosecone attached to the elongate catheter body and a hinge between the nosecone and the elongate catheter body configured, when hinged, to expose the cutter.

15. The atherectomy catheter of claim 14, wherein the drive shaft is configured such that proximal movement of the drive shaft deflects the cutter and activates the hinge to expose the cutter.

16. The atherectomy catheter of claim 12, further comprising an imaging element attached to the cutter.

17. The atherectomy catheter of claim 16, wherein the imaging element is an optical coherence tomography imaging element.

18. The atherectomy catheter of claim 10, wherein the predetermined curved shape comprises a first inflection point corresponding to the first stiffening member, and a second inflection point corresponding to the second stiffening member.

19. The atherectomy catheter of claim 18, wherein the first and second inflection points have opposite curvatures.

20. The atherectomy catheter of claim 12, wherein the distal end is configured to pivot with respect to the main shaft between a closed position and an open position, wherein a rotational axis of the rotatable cutter is parallel to the distal end when the catheter body is in the closed position, and wherein the rotational axis of the rotatable cutter is non-parallel to the distal end when the catheter body is in the open position.

21. An atherectomy catheter comprising:

an elongate catheter body having a distal end and a main shaft, the distal end configured to pivot with respect to the main shaft between a closed position and an open position, the main shaft having first and second stiffening members therein that are aligned with a longitudinal axis of the main shaft, the first stiffening member axially and radially offset from the second stiffening member;

a rotatable cutter having a distal cutting edge near the distal end of the elongate catheter body, wherein a rotational axis of the rotatable cutter is parallel to the distal end when the catheter body is in the closed position, and wherein the rotational axis of the rotatable cutter is non-parallel to the distal end when the catheter body is in the open position; and a drive shaft extending through the elongate catheter body and connected to the rotatable cutter, wherein the drive shaft is configured such that axial movement of the drive shaft compresses portions of the elongate catheter body surrounding the first and second stiffening members to cause the elongate catheter body to assume a predetermined s-shape when the catheter body is in the closed position.

22. The atherectomy catheter of claim 21, wherein the distal end of the catheter body comprises a nosecone configured to store tissue therein.

23. The atherectomy catheter of claim 21, further comprising an imaging element attached to the cutter.

* * * * *